United States Patent
Chen et al.

(10) Patent No.: US 11,109,548 B2
(45) Date of Patent: Sep. 7, 2021

(54) APPLICATION OF HIGH FLAVONOID ELITE GERMPLASM 'CSR6R6-777' IN BREEDING FOR FUNCTIONAL APPLE

(71) Applicant: Shandong Agricultural University, Shandong (CN)

(72) Inventors: Xuesen Chen, Shandong (CN); Nan Wang, Shandong (CN); Shenghui Jiang, Shandong (CN); Haifeng Xu, Shandong (CN); Yicheng Wang, Shandong (CN); Zhiquan Mao, Shandong (CN); Yuanmao Jiang, Shandong (CN)

(73) Assignee: SHANDONG AGRICULTURAL UNIVERSITY, Shandong (CN)

( * ) Notice: Subject to any disclaimer, the term of this patent is extended or adjusted under 35 U.S.C. 154(b) by 50 days.

(21) Appl. No.: 15/761,069

(22) PCT Filed: Sep. 26, 2017

(86) PCT No.: PCT/CN2017/103348
§ 371 (c)(1),
(2) Date: Mar. 16, 2018

(87) PCT Pub. No.: WO2018/107852
PCT Pub. Date: Jun. 21, 2018

(65) Prior Publication Data
US 2020/0267919 A1    Aug. 27, 2020

(30) Foreign Application Priority Data
Dec. 12, 2016 (CN) .......................... 201611138572.1

(51) Int. Cl.
*A01H 1/04* (2006.01)
*A01H 1/02* (2006.01)
*C12Q 1/6895* (2018.01)

(52) U.S. Cl.
CPC ................. *A01H 1/04* (2013.01); *A01H 1/02* (2013.01); *C12Q 1/6895* (2013.01)

(58) Field of Classification Search
None
See application file for complete search history.

(56) References Cited

FOREIGN PATENT DOCUMENTS

| CN | 103314840 A | 9/2013 |
| CN | 105123497 A | 12/2015 |
| CN | 105359963 A | 3/2016 |
| CN | 106718835 A | 5/2017 |
| JP | 2012044935 A | 3/2012 |
| SU | 1029926 A1 | 7/1983 |
| WO | WO 2008/017842 A1 | 2/2008 |

OTHER PUBLICATIONS

Wang et al Jul. 14, 2015 PLOS ONE 1-20 (Year: 2015).*
International Search Report received in PCT Application No. PCT/CN2017/103348, dated Dec. 6, 2017.
Written Opinion received in PCT Application No. PCT/CN2017/103348, dated Dec. 6, 2017.
Chen Xue-sen et al., "Genetic Variation of $F_1$ Population Between *Malus sieversii f. neidzwetzkyana* and Apple Varieties and Evaluation on Fruit Characters of Functional Apple Excellent Strains" Dec. 31, 2014. 47(11) Scientia Agricultura Sinica. 2193-2204.

* cited by examiner

*Primary Examiner* — Brent T Page
(74) *Attorney, Agent, or Firm* — Knobbe, Martens, Olson & Bear, LLP (57) ABSTRACT

The present invention discloses an application of high-flavonoid elite germplasm CSR6R6-777 in apple breeding. The present invention seeks to protect use of an apple (*Malus domestica*) CSR6R6-777 in apple breeding. The deposition number of the apple (*Malus domestica*) CSR6R6-777 is CGMCC NO. 12468. The purpose of the breeding is to obtain an apple germplasm with excellent traits. The apple germplasm with excellent traits is an apple plant that meets the (a) and/or (b) and/or (c) and/or (d): (a) fully red-fleshed; (b) high-flavonoid content in the flesh; (c) high anthocyanin content in the flesh; (d) high antioxidant capacity of the flesh. The present application has great value for functional apple breeding.

13 Claims, 5 Drawing Sheets
(4 of 5 Drawing Sheet(s) Filed in Color)
Specification includes a Sequence Listing.

Xinjiang red-fleshed apple       'Red Fuji'       'CSR6R6-777'

APPLICATION OF HIGH FLAVONOID ELITE GERMPLASM 'CSR6R6-777' IN BREEDING FOR FUNCTIONAL APPLE

CROSS-REFERENCE TO RELATED APPLICATIONS

This application is a U.S. National Phase Application of PCT International Application No. PCT/CN2017/103348, filed on Sep. 26, 2017, designating the United States of America, which is an International Application of and claims the benefit of priority to Chinese Patent Application No. 201611138572.1, filed on Dec. 12, 2016.

TECHNICAL FIELD

The present invention relates to use of high-flavonoid elite germplasm 'CSR6R6-777' in functional apple breeding.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 32505852_1.txt, the date of creation of the ASCII text file is Mar. 25, 2020, and the size of the ASCII text file is 2.79 KB.

BACKGROUND

"Medicine and food being originated from a same source" is a trend of development, "eating for nutrition, eating for health" has become a general consensus among the people. Therefore, it is of great significance to carry out functional apple breeding to improve the human health.

Functional apple breeding is an effective integration and balance of multiple quality traits (genes). In order to improve and perfect breeding of new varieties and improve breeding efficiency, the present research group took three measures: firstly, in view of studies on genetic variation of traits such as total phenolic content of fruit of a hybrid F1 population of Xinjiang red-fleshed apple crossed with cultivated apple, "three-selection, two-advancing and one-promotion" apple breeding method (Patent No. 201310205419.6) was proposed and implemented, in which the breeding efficiency was increased significantly. Secondly, multiple parental crosses and repeated backcrosses were carried out using cultivated apple varieties with complex genetic backgrounds such as 'Gala', 'America 8', 'Hanfu' and 'Fuji', etc and Xinjiang red-fleshed apple (*M. sieversii f. niedzwetzkyana*) for quality breeding. So far, 40 separate populations of the first backcrossing generation and the second backcrossing generation have been established, and 40,000 hybrid seedlings were planted, and two patents for invention of breeding technology were granted: "fruit tree multi-provenance quality seed breeding method (Patent No.: ZL 201510428448.8)" and the "method for cultivating easy-coloring apple variety (Patent No.: ZL 201510890141.X)". Thirdly, studies on the quality traits evaluation and development mechanism were carried out using the progeny with substantially stable traits as a test material in a timely manner, and many important progresses had been made. At present, a highly efficient breeding system for apple, in which traditional crosses and biotechnology were combined associatedlly, was created, a batch of new varieties and elite germplasms were created, and a highly efficient cultivation system for new varieties of apples was developed. More than 10 patents for invention were granted and submitted, and 16 new varieties (strains) were cultivated; 120 related research papers were published, in which there were more than 20 SCI papers, all of which are leading the international similar researches.

DISCLOSURE OF THE INVENTION

The present invention provides a use of high flavonoid elite germplasm 'CSR6R6-777' in functional apple breeding.

The high flavonoid elite germplasm 'CSR6R6-777' provided by the present invention, also called apple (*Malus domestica*) CSR6R6-777, was deposited in the China General Microbiological Culture Collection Center (abbreviated as CGMCC, address: No. 3, Courtyard No. 1, Beichenxi Road, Chaoyang District, Beijing, Institute of Microbiology, Chinese Academy of Sciences) on Dec. 8, 2016 with an accession number of CGMCC NO. 12468. Apple (*Malus domestica*) CSR6R6-777 CGMCC NO. 12468 was called apple CSR6R6-777 for short. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from the date of deposit. The deposit will be made available by CGMCC under the terms of the Budapest Treaty, and subject to an agreement between Applicant and CGMCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strains is not to be construed as a license to practice the invention in contravention of the rights granted under the authority of any government in accordance with its patent laws.

The present invention seeks to protect use of apple CSR6R6-777 in apple breeding. In the use, the apple CSR6R6-777 was used as one of the parent plants. In the use, apple CSR6R6-777 was used as a paternal parent plant. The purpose of the breeding is to obtain fully red-fleshed plants.

The purpose of the breeding is to obtain fully red-fleshed plants with R6R1 genotype. The purpose of the breeding is to obtain an apple germplasm with excellent traits. The apple germplasm with excellent traits is an apple plant that meets (a) and/or (b) and/or (c) and/or (d): (a) fully red-flushed; (b) high flavonoid content in the flesh; (c) high anthocyanin content in the flesh; (d) high antioxidant capacity of the flesh. The apple germplasm with excellent traits is R6R1 genotype. The high flavonoid content in the flesh means that the content of the flavonoids of fresh weight of the flesh is 200 mg per kilogram or more. The high anthocyanin content in the flesh means that the content of the anthocyanin of fresh weight of the flesh is 30 mg per kilogram or more. The high antioxidant capacity of the flesh means that the antioxidant capacity (also called antioxidant content) of fresh weight of the flesh is 1 µmol per kilogram or more.

The present invention also protects an apple breeding method, which comprises the steps:

(1) crossing an apple variety A with an apple variety B to obtain hybrid seeds; the apple variety A is apple CSR6R6-777; the apple variety B is an apple variety except apple variety A;

(2) sowing and seedling the hybrid seed obtained in step (1) to obtain seedlings;

(3) transplanting the seedlings obtained in the step (2) to a field, skipping bagging after fruiting, and after screening, a target plant is obtained.

The method for crossing an apple variety A with an apple variety B is as follows: the apple variety B after removal of stamens is pollinated with pollen of the apple variety A.

In the step (2), before the sowing, the hybrid seeds are subjected to a stratification of 1-3° C. to break dormancy. The time of the stratification may specifically be 60 days.

In the step (2), conditions for the seedling are: 25° C., 12 hours of illumination per day with an intensity of illumination of 3000 1x, and nutrient solution is poured once every 7-10 days from the seed germination.

In the step (2), conditions for the seedling are specifically as follows: the hybrid seeds are sown and cultivated in a nutrient bowl (3-5 seeds in each nutrient bowl) with cultivation matrix until the seedlings is 8-15 cm in height and lignified at root collar (usually 2-3 months after sowing), and then the seedlings are transplanted to a new nutrient bowl (one transplant per nutrient bowl) for cultivation. Conditions for the cultivation are: 25° C., 12 hours of illumination per day (intensity of illumination 3000 1x), and nutrient solution (a large quantity of elements stock solution of MS minimal medium is diluted with water to 10 times to be the nutrient solution) is poured once every 7-10 days from the seed germination, 40-50 ml per nutrient bowl for each time.

In the step (3), a method for cultivation and management in the field is as follows: the field for planting the seedlings is applied with 6000 kg of organic fertilizer per mu and watered to be sunk. After the seedlings are planted, the field is appied 6000 kg of organic fertilizer per mu again and watered in time. The organic fertilizer may specifically be fully-matured cow dung.

The target plant is a fully red-fleshed plant.

The target plant is a fully red-fleshed plant with R6R1 genotype.

The target plant is an apple plant that meets (a) and/or (b) and/or (c) and/or (d): (a) fully red-fleshed; (b) high flavonoid content in the flesh; (c) high anthocyanin content in the flesh; (d) high antioxidant capacity of the flesh. The apple germplasm with excellent traits is R6R1 genotype. The high flavonoid content in the flesh means that the content of the flavonoids per kilogram of fresh weight of the flesh is 200 mg or more. The high anthocyanin content in the flesh means that the content of the anthocyanin per kilogram of fresh weight of the flesh is 30 mg or more. The high antioxidant capacity of the flesh means that the antioxidant capacity (also called antioxidant content) per kilogram of fresh weight of the flesh is 1 µmol or more.

In the method, in the fourth year after transplanting, a trunk of the seedling is girdled 20 cm away from the ground, and the width of the girdling is 0.5-1.0 cm, reaching the xylem.

In the method, in the fifth year after transplanting, the following operations are carried out in the full flowering phase of the seedling: only the central flower among 5 flowers of each inflorescence is retained, and the rest are all removed.

In the method, the target plant is obtained in the fifth year after transplanting.

The apple variety B is an apple variety with R1R1 genotype.

The apple variety B is specifically 'Gala' apple or 'Fuji' apple.

A method for identifying the R1R1 genotype is as follows: taking an apple from an apple plant to be tested, extracting genomic DNA from the apple flesh, carrying out PCR amplification by using a specific primer pair with the genomic DNA as a template, and then judging the genotype according to the following criterion: if there is a 386 bp DNA fragment and not a 497 bp DNA fragment in the amplified product, the apple plant to be tested is one with R1R1 genotype. A method of identifying the R1R1 genotype is as follows: taking an apple from an apple plant to be tested, extracting genomic DNA from the apple flesh, carrying out PCR amplification by using a specific primer pair with the genomic DNA as a template, and then judging the genotype according to the following criterion: if there is one band with a size of 386 bp for PCR amplification product, the apple plant to be tested is one with R1R1 genotype.

A method of identifying the R6R1 genotype is as follows: taking an apple from an apple plant to be tested, extracting genomic DNA from apple flesh, carrying out PCR amplification by using a specific primer pair, with the genomic DNA as a template, and then judging the genotype according to the following criterion: if there are both a 497 bp DNA fragment and a 386 bp DNA fragment for the amplified product, the apple plant to be tested is one with R6R1 genotype. A method of identifying the R6R1 genotype is as follows: taking an apple from an apple plant to be tested, extracting genomic DNA from apple flesh, carrying out PCR amplification by using a specific primer pair with the genomic DNA as a template, and then judging the genotype according to the following criterion: if there are two bands with a size of 497 bp and a size of 386 bp, respectively for the PCR amplified products, the apple plant to be tested is one with R6R1 genotype.

The specific primer pair consists of F1 and R1; the F1 is a single-stranded DNA molecule shown in SEQ ID NO: 1 of the Sequence listings; the R1 is a single-stranded DNA molecule shown in SEQ ID NO: 2 of the Sequence listings.

The present invention also protects use of apple CSR6R6-777 for manufacturing of food with apple fruit as raw material. The food with apple fruits as raw material comprises fresh apples, dried apples, apple jam and the like.

The present invention also protects use of apple CSR6R6-777 for manufacturing of food processing product with apple fruit as raw material. The food processing products with apple fruits as raw material comprise apple wine, apple vinegar and the like.

DESCRIPTION OF THE DRAWINGS

The patent or application file contains at least one drawing executed in color. Copies of this patent or patent application publication with color drawing(s) will be provided by the Office upon request and payment of the necessary fee.

THE BEST MODE FOR CARRYING OUT THE INVENTION

The following examples will provide a better understanding of the present invention, but do not limit the present invention. The experimental methods in the following examples, unless otherwise specified, are conventional methods. The test materials used in the following examples, unless otherwise specified, are purchased from conventional biochemical reagents stores. Three times of repeated experiments are set for the quantitative test in the following examples, and the results are averaged. The structural formula of rutin is as follows:

The structural formula of Trolox is as follows:

A method for preparing 0.5% hydrochloric acid methanol solution is: 0.5 parts by volume of 35% concentrated hydrochloric acid is mixed with 99.5 parts by volume of methanol.

A method for preparing 1% hydrochloric acid methanol solution is: 1 part by volume of 35% concentrated hydrochloric acid is mixed with 99 parts by volume of methanol.

A method for preparing 80% acetone solution: 4 parts by volume of acetone is mixed with 1 part by volume of water.

A method for identifying apple plants to be R1R1 genotype, R6R6 genotype or R6R1 genotype is as follows: taking an apple from an apple plants to be tested, extracting genomic DNA from the apple flesh, carrying out PCR amplification by using primers consisting of F1 and R1 with the genomic DNA as a template, and then judging the genotype according to the following criterion: if there is one band for the PCR amplified product with a size of 497 bp, the apple plant to be tested is one with R6R6 genotype; if there is one band for the PCR amplified product with a size of 386 bp, the apple plant to be tested is one with R1R1 genotype; if there are two bands for the PCR amplified product with a size of 497 bp and 386 bp respectively, the apple plant to be tested is one with R6R1 genotype.

F1 (SEQ ID NO: 1): 5'-GGTGGTCAAAGATGTGTGTTGT-3';

R1 (SEQ ID NO: 2): 5'-TTTGCCTGCTACCCACTTCA-3'.

Reference to 'Red Fuji' apple and 'Gala' apple: Chen Xuesen, Xin Peigang et al., Effect of Delicious and golden Delicious on the breeding and selection of new apple varieties, Journal of Shandong Agricultural University, 1994, 25(2): 236-248. After testing, both 'Red Fuji' apple and 'Gala' apple are the ones with R1R1 genotype.

Reference to 'RedLove' apple: Zheng Jiwen, Yao Shaoqun, Liu Shuzhen, red-fleshed apple new variety "RedLove", Northwest Horticulture, 201304.

Example 1. Identification of Apple Elite Germplasm 'CSR6R6-777'

I. Acquirement of 'CSR6R6-777'

Xinjiang red flesh apple as a parent plant was crossed with white flesh apple cultivars such as 'Red Fuji'. According to the Mendel's law, Xinjiang red flesh apple (R6R1 genotype) was crossed with white flesh apple cultivars such as 'Red Fuji' (R1R1 genotype), the progeny population should have red flesh phenotype (R6R1 genotype):white flesh phenotype (R1R1 genotype)=1:1. However, three single plants with R6R6 genotype were found in the hybrid F1 population (868 plants).

The three single plants all had the following phenotypes: leaves, flowers, peels and flesh were amaranth in all developmental stages. The stem of one single plant was also amaranth, and this single plant was named as 'CSR6R6-777'. The stems of the other two plants were light red, and they were named as control plant I and control plant II, respectively.

A single plant with R1R1 genotype (named as control plant A) and a single plant with R6R1 genotype plant (named as control plant B) was randomly selected from the hybrid F1 population.

Figure 1:
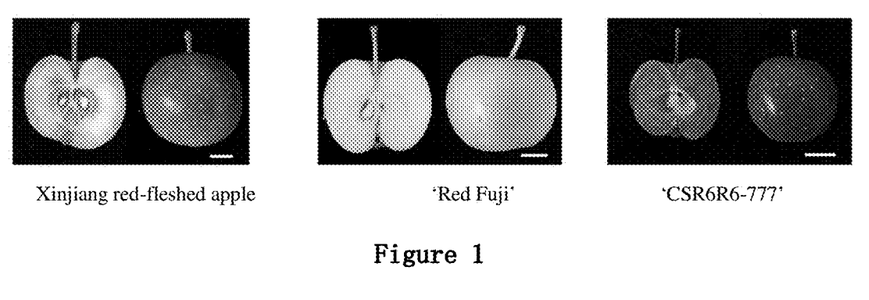
FIG. 1 shows phenotype comparison of the fruits from Xinjiang red flesh apple, 'Red Fuji' and 'CSR6R6-777'.

Comparison of phenotypes of fruits from Xinjiang red flesh apple, 'Red Fuji' and 'CSR6R6-777' was shown FIG. 1.

II. Deposit of 'CSR6R6-777'

'CSR6R6-777', also called apple (*Malus domestica*) CSR6R6-777, was deposited in the China General Microbiological Culture Collection Center (CGMCC, address: No. 3, Courtyard No. 1, Beichenxi Road, Chaoyang District, Beijing, Institute of Microbiology, Chinese Academy of Sciences) on Dec. 8, 2016, the accession number was CGMCC NO. 12468.

III. Analysis of Expression of Flavonoid Biosynthesis Related Genes

'CSR6R6-777', control plant A and control plant B were used as plants to be tested. Apples were taken from the plants to be tested, and total RNA was extracted from the apple flesh. Expression of genes (CHS gene, F3H gene, ANS gene, LAR gene, FLS gene) of key enzymes and a gene (MYB10 gene) of key transcription factor in flavonoid synthesis pathway were detected by real-time quantitative RT-PCR. Primer pairs used to detect CHS gene were as follows:

```
                                        (SEQ ID NO: 3)
    CHS-F: 5'- GGAGACAACTGGAGAAGGACTGGAA-3';

(SEQ ID NO: 4)
    CHS-R: 5'- CGACATTGATACTGGTGTCTTC-3'.
```

Primer pairs used to detect F3H gene were as follows:

```
                                        (SEQ ID NO: 5)
    F3H-F: 5'- TGGAAGCTTGTGAGGACTGGGGT-3';

(SEQ ID NO: 6)
    F3H-R: 5'- CTCCTCCGATGGCAAATCAAAGA-3'.
```

Primer pairs used to detect ANS gene were as follows:

```
                                        (SEQ ID NO: 7)
    ANS-F: 5'- CCAAGTGAAGCGGGTTGTGCT-3';

(SEQ ID NO: 8)
    ANS-R: 5'- CAAAGCAGGCGGACAGGAGTAGC -3'.
```

Primer pairs used to detect LAR gene were as follows:

```
                                        (SEQ ID NO: 9)
    LAR-F: 5'- CACCGTCAAGTCCTTCAA-3';

(SEQ ID NO: 10)
    LAR-R: 5'- ACCTCTTAACTGTACCAACTG -3'.
```

Primer pairs used to detect FLS gene were as follows:

```
                                        (SEQ ID NO: 11)
    FLS-F: 5'- AACCACTGTGAACAAGGATA-3';

(SEQ ID NO: 12)
    FLS-R: 5'- CATAGTCGCCGTACTTCTT-3'.
```

Primer pairs used to detect MYB10 gene were as follows:

```
                                        (SEQ ID NO: 13)
    MYB10-F: 5'-TGCCTGGACTCGAGAGGAAGACA-3';

(SEQ ID NO: 14)
    MYB10-R: 5'- CCTGTTTCCCAAAAGCCTGTGAA-3'.
```

MdActin was used as an internal control; data analysis was performed using $2^{-\Delta\Delta CT}$ method (Livak & Schmittgen, 2001).

Figure 2:
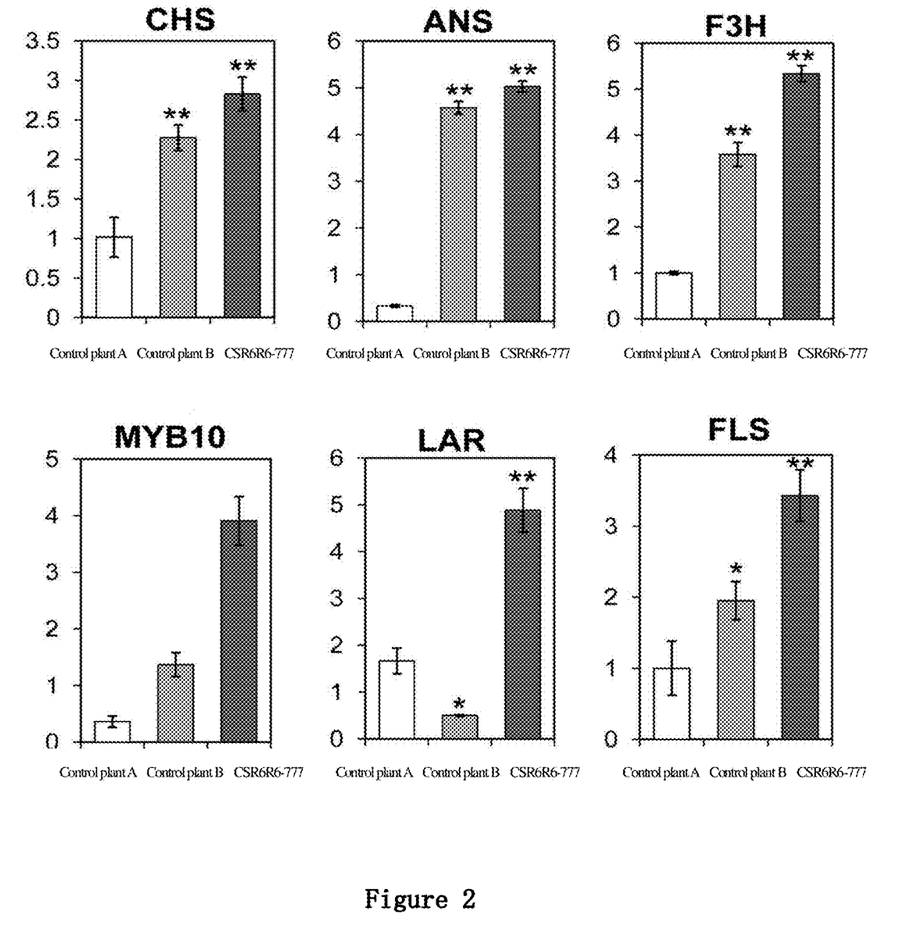
FIG. 2 shows the relative expressions of each gene.

Relative expression of each of genes was shown in FIG. 2. The expression of each of genes in 'CSR6R6-777' was significantly higher than that of the corresponding genes in control plant A and control plant B. The results showed that 'CSR6R6-777' had a strong ability to synthesize flavonoid.

IV. Analysis of Flavonoid Content

'CSR6R6-777', control plant A and control plant B were used as plants to be tested.
1. Taking apples from the plants to be tested, and taking flesh from the apples.
2. Grinding the fleshes obtained in step 1 in liquid nitrogen to obtain powder.
3. Weighing 2 g of powder obtained in step 2, adding 5 mL of 0.5% hydrochloric acid methanol solution, keeping the mixture stand and extracting it at 4° C. for 2 hours, then centrifugating the mixture at 8000 rpm for 20 mins, collecting the supernatant and the residue, respectively.
4. Adding 5 mL of 0.5% hydrochloric acid methanol solution to the residue obtained in step 3, keeping the mixture stand and extracting it at 4° C. for 1 h, then performing centrifugation at 8000 rpm for 20 mins, collecting the supernatant.
5. Mixing the supernatant obtained in Step 3 and the supernatant obtained in Step 4 to obtain a mixed solution.
6. Removing methanol from the mixed solution obtained in step 5 by rotary evaporation at 37° C., dissolving the residue with 2-3 ml methanol, and then performing centrifugation at 8000 rpm for 20 mins, collecting the supernatant.
7. Adding methanol to the supernatant obtained in step 6 to make the volume to be 5 ml, and then filtering the solution with 0.45 μm filter membrane, collecting the filtrate.
8. Subjecting the filtrate obtained in step 7 to HPLC-MS analysis.

Conditions for Liquid Chromatography:
WATERS ACQUITY UPLC chromatography was used, with a chromatographic column of BEH C18 column (100 mm×2.1 mm), a particle size of filler of 1.7 μm; column temperature 45° C.; injection volume of 1 μL;
the mobile phase was a mixture of liquid A and liquid B, the flow rate was 0.3 mL/min; liquid A was acetonitrile, liquid B was 0.2% (volume fraction) formic acid in water; the volume fraction of liquid A in the mobile phase was 5% at 0-0.1 min;
the volume fraction of liquid A in the mobile phase increased linearly from 5% to 20% at 0.1-20 mins; the volume fraction of liquid A in the mobile phase increased linearly from 20% to 80% at 20-22 mins; the volume fraction of liquid A in the mobile phase decreased linearly from 80% to 5% at 22-22.1 mins; the volume fraction of liquid A in the mobile phase was 5% at 22.1-25 mins.

Conditions Mass Spectrometry
Mass spectrometer WATERS MALDI SYNAPT Q-TOF MS, ESI ionization source, electrospray ionization positive ion acquisition mode (ESI+); scan range 100-1500 m/z; capillary voltage 3.5 kV, cone voltage 30 V; source temperature 100° C., desolventizing temperature 300° C.; desolvation gas flow is 500 L/h.

Figure 3:
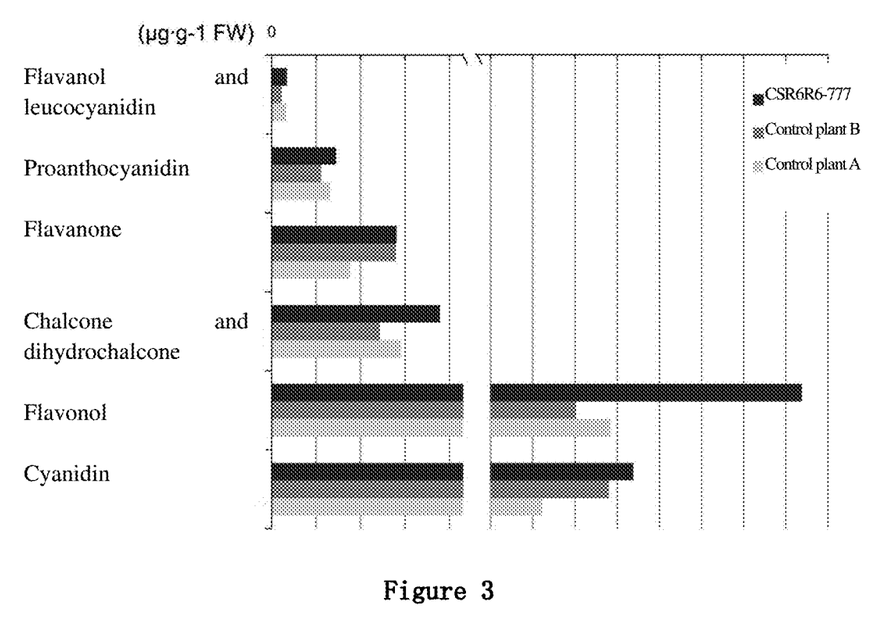
FIG. 3 shows the content of flavanol and leucocyanidin, the content of proanthocyanidin, the content of flavanone, the content of chalcone and dihydrochalcone, the content of flavonol, and the content of cyanidin in apple flesh.

The content of flavanol and leucocyanidin, the content of proanthocyanidin, the content of flavanone, the content of chalcone and dihydrochalcone, the content of flavonol, the content of cyanidin per gram of fresh weight of the apple flesh were shown in FIG. 3. The content of proanthocyanidin, the content of chalcone and dihydrochalcone, the content of flavonol, the content of cyanidin in the flesh of apple 'CSR6R6-777' were significantly higher than those in control plant A and control plant B.

Figure 4:
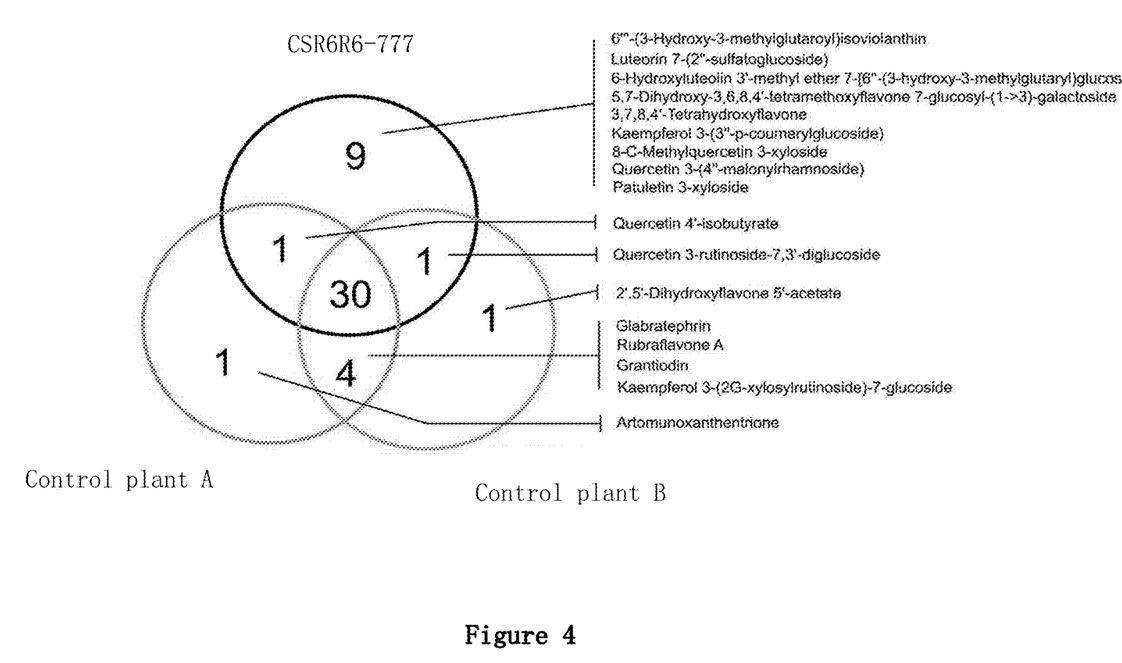
FIG. 4 shows the results of precise identification of the flavonol in apple flesh.

Flavonol in the apple flesh was accurately identified, and the results were shown in FIG. 4. The flesh of apple 'CSR6R6-777' comprises 41 flavonol substances, 9 substances of which were characteristic and absent in apple flesh of control plant A and control plant B. The 9 flavonol substances characteristic for the flesh of apple 'CSR6R6-777' were shown in Table 1. Detection methods for the 9 flavonol substances in Table 1 all belonged to the detection methods of component and content of flavonoids (reference: Chen Xuesen, Zhang Jing, Liu Daliang, et al., Genetic Variation of F1 Population Between *Malus sieversii f. neidzwetzkyana* and Apple Varieties and Evaluation on Fruit Characters of Functional Apple Excellent Strains [J]. Scientia Agricultura Sinica, 2014, 47 (11): 2193-2204).

TABLE 1

| Substances | Content (μg/g fresh weight) |
| --- | --- |
| 6'''-(3-Hydroxy-3-methylglutaroyl)isoviolanthin | 55.25422315 |
| Luteorin 7-(2''-sulfatoglucoside) | 12.83562724 |
| 6-Hydroxyluteolin 3'-methyl ether 7-[6''-(3-hydroxy-3-methylglutaryl)glucoside] | 25.20263117 |
| 3,7,8,4'-Tetrahydroxyflavone | 517.7717278 |
| Kaempferol 3-(3''-p-coumarylglucoside) | 55.32757109 |
| 8-C-Methylquercetin 3-xyloside | 3905.558993 |
| Quercetin 3-(4''-malonylrhamnoside) | 21.48360807 |
| Patuletin 3-xyloside | 94.37930534 |
| 5,7-Dihydroxy-3,6,8,4'-tetramethoxyflavone 7-glucosyl-(1->3)-galactoside | 68.8005295 |

The above result showed that 'CSR6R6-777' had a strong ability to synthesize flavonoids, the flesh was rich in flavonoid and contained special flavonols components. 'CSR6R6-777' was an elite germplasm for breeding functional apple varieties.

Example 2. Fully Red-Fleshed Plants were Obtained by a Cross Using 'CSR6R6-777' as a Parental Plant I. Breeding Fully Red-Fleshed Plants from Hybrid Progeny
1. Backcross (in Muping District, Yantai, Shandong Province)

In April 2011, 'Gala' apple after removal of stamens was pollinated with pollen of 'CSR6R6-777', and BC1 hybrid seeds were harvested. The BC1 hybrid seeds were washed and stored in a fresh-keeping chamber at 1-3° C. for stratification for about 60 days (which aims at breaking seed dormancy by meeting chilling requirement).

2. Greenhouse Seedling (in Tai'an, Shandong Province)

In December 2011, the BC1 hybrid seeds obtained in step 1 were sowed and cultivated in a nutrient bowl (3-5 seeds in each nutrient bowl) with cultivation matrix until the seedlings was 8-15 cm in height and lignified at the root collar (usually 2-3 months after sowing), and then the seedlings were transplanted to a new nutrient bowl (one transplant per nutrient bowl) for cultivation. Conditions for the cultivation in this step were: 25° C., 12 hours of illumination per day (intensity of illumination 3000 1x), and nutrient solution (a large quantity of elements stock solution of MS minimal medium was diluted with water to 10 times to be the nutrient solution) was poured once every 7-10 days from the seed germination, 40-50 ml per nutrient bowl each time.

3. Planting the Hybrid Seedlings (in Guan County, Shandong Province)

In February 2012, the selective nursery (the field) for planting the seedlings was applied with 6000 kg of organic fertilizer (fully-matured cow dung used in this Example) per mu in and watered to be sunk. In April 2012, 3,600 seedlings obtained in step 2 were planted in the selective nursery. In April 2012, the selective nursery in which the seedlings were planted was applied with 6000 kg of organic fertilizer (fully-matured cow dung used in this Example) per mu again and watered in time.

4. Girdling Treatment for the Hybrid Seedlings

In May 2015, a trunk of each of the seedlings was girdled 20 cm away from the ground, and the width of the girdling was 0.5-1.0 cm, reaching the xylem. The purpose of this operation was to promote the accumulation of nutrients and flower bud differentiation, so as to shorten the juvenile phase and fruit early.

5. Flower and Fruit Management

From April to May, 2016, flowers were thinned in the full flowering phase of each of seedlings (only the central flower among 5 flowers of each of inflorescences was retained, and the rest were all removed). Young fruits were skipping bagged and subjected to routine management.

6. Obtaining Fully Red-Fleshed Plant

In August 2016, five fully red-fleshed plants were screened and bred from backcross progeny population: 'Zixia 1', 'Zixia 2', 'Zixia 3', 'Hongxin11' and 'Hongxin16'.

II. Phenotype Characteristic

Figure 5:
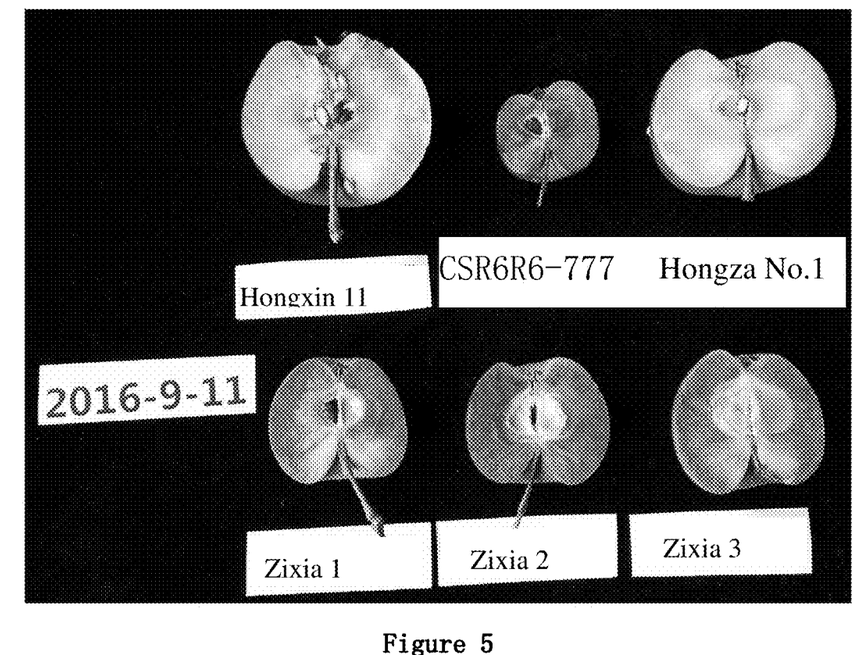
FIG. 5 is a photo of apple fruits from some progeny plants.
Figure 6:
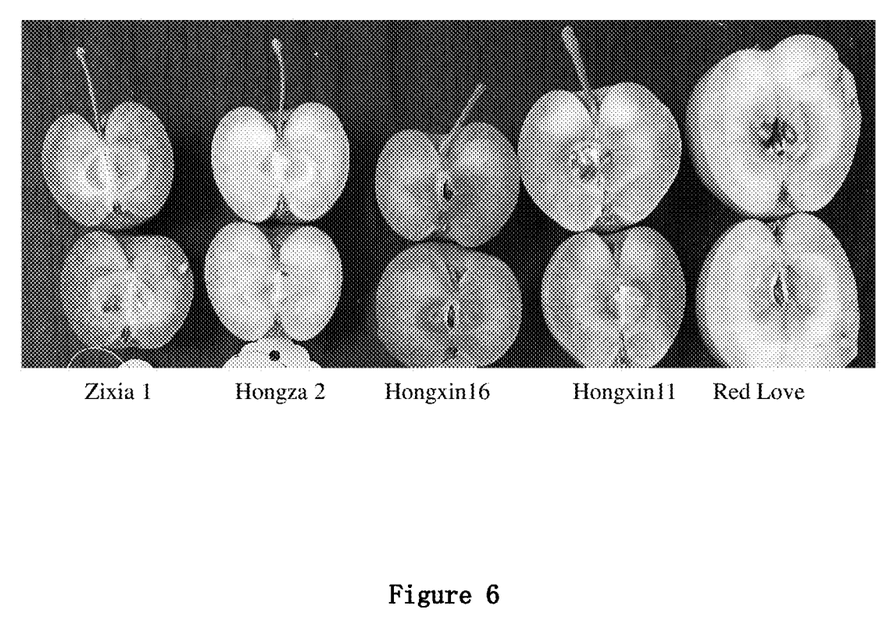
FIG. 6 is a photo of apple fruits from some progeny plants.
Figure 7:
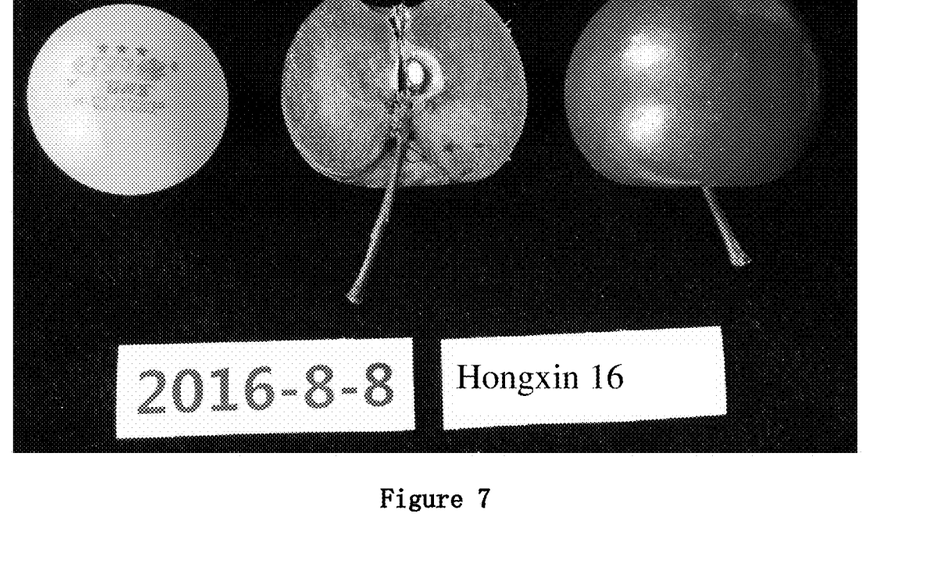
FIG. 7 is a photo of apple fruits from some progeny plants.

The fruit characteristics of the apples grown on the 5 plants were shown in FIGS. 5, 6 and 7.

III. Genotype

The genotypes of the 5 plants were as follows:
'Hongxin 11', R6R1 genotype;
'Hongxin 16', R6R1 genotype;
'Zixia 1', R6R1 genotype;
'Zixia 2', R6R1 genotype;
'Zixia 3', R6R1 genotype.

Figure 8:
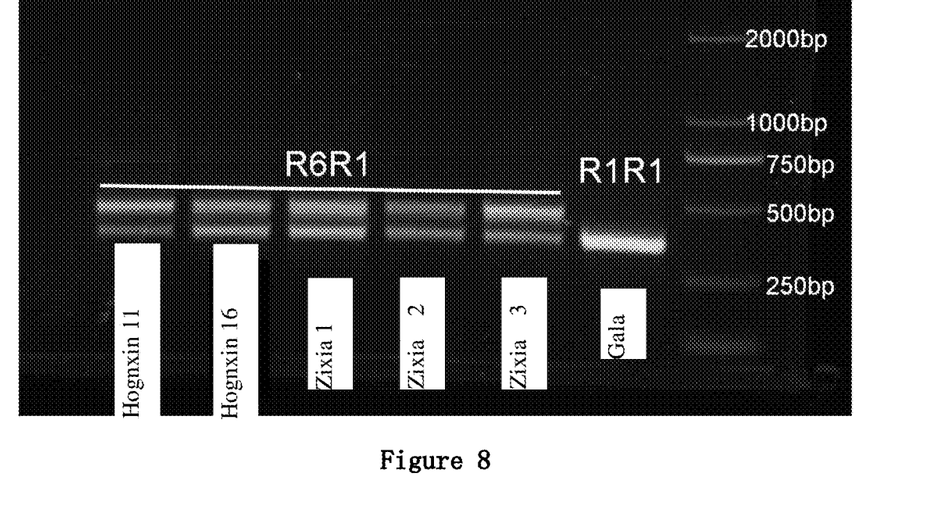
FIG. 8 shows the results of genotype identification of 'Hongxin 11', 'Hongxin 16', 'Zixia 1', 'Zixia 2', 'Zixia 3' and 'Gala'.

Identification map was shown in FIG. 8.

The results showed that fully red-fleshed plants with the R6R1 genotype could be selected from the segregating population of 'CSR6R6-777' hybrid progeny.

IV. Analysis for flavonoid content, anthocyanin content and antioxidant capacity Materials to be tested: apples grown on 'Hongxin 11', apples grown on 'Hongxin16', apples grown on 'Zixia 1', apples grown on 'Zixia 2', apples grown on 'Zixia 3', apples grown on 'CSR6R6-777', and apples grown on 'Gala'.

1. Determination of Flavonoid Content (1) Grinding 1 g flesh in liquid nitrogen, then adding 10 ml of 65% (volume percentage) ethanol aqueous solution pre-cooled at 4° C. and mixing them well, keeping the mixture stand and extracting it in dark at 4° C. for 4 h, then perfoming centrifugation at 12000 rpm for 20 mins, and collecting the supernatant.

(2) Adding 0.5 ml supernatant obtained in step (1) to a test tube, then adding sequently 1 mL 5 g/100 ml $NaNO_2$ aqueous solution, 1 ml 10 g/100 ml $AL(NO_3)_3$ aqueous solution, 4 mL 2 M NaOH aqueous solution and mixing them well, keeping the mixture stand for 15 mins and centrifuging it at 8000 rpm for 10 mins, collecting the supernatant and then measuring the absorbance at 510 nm.

Standard curve was plotted using rutin (Sigma chemical, ST, Loiuis, USA) as a standard sample.

2. Determination of Anthocyanin Content (1) Grinding 0.5 g flesh in liquid nitrogen, then adding 5 ml 1% hydrochloric acid methanol solution pre-cooled at 4° C., keeping the mixture stand and extracting it in the dark at 4° C. for 24 hours.

(2) Adding 4 ml KCl buffer or 4 ml NaAC buffer to 1 ml extract obtained in step (1) and mixing them well, keeping the mixture stand and extracting it in the dark at 4° C. for 15 mins, then performing centrifugationg at 8000 r/min for 10 mins, collecting the supernatant.

KCl buffer (pH=1, 0.025 M): 1.86 g KCl was dissolved in 980 ml distilled water, pH was adjusted to 1.0 with concentrated hydrochloric acid, the solution was transferred to a 1 L volumetric flask, and distilled water was added to make the volume to be 1 L.

NaAC buffer (pH=4.5, 0.4 M): 54.43 g NaAC was dissolved in 960 ml distilled water, pH was adjusted to 4.5 with concentrated hydrochloric acid, the solution was transferred to a 1 L volumetric flask, and distilled water was added to make the volume to be 1 L.

(3) Taking the supernatant obtained in step (2) and measuring the absorbance at 510 nm and 700 nm, respectively.

Anthocyanin content(mg/g)=
  $\Delta A*5*0.005*1000*449.2/(26900*0.5)$;

$\Delta A=(A_{510\ nm}-A_{700\ nm})_{pH\ 1.0}-(A_{510\ nm}-A_{700\ nm})_{pH\ 4.5}$.

3. Determination of Antioxidant Capacity (1) Grinding the flesh in liquid nitrogen to obtain powder.

(2) Weighing 10 g powder obtained in step (1), adding 50 mL 80% acetone solution, keeping the mixture stand and extracting it at 4° C. for 1 h, then performing centrifugation at 8000 rpm for 10 mins, and collecting the supernatant.

(3) Adding 50 mL 80% acetone solution to the residue of step (2), keeping the mixture stand and extracting it at 4° C. for 1 h, then performing centrifugation at 8000 rpm for 10 mins, and collecting the supernatant.

(4) Combining the supernatant obtained in step (2) and the supernatant obtained in step (3) to obtain a mixed solution.

(5) Removing acetone from the mixed solution obtained in step (4) by rotary evaporation at 40° C., centrifuguing the residue at 5000 rpm, collecting the supernatant, and adding the deionized water to make a volume to be 20 mL, so as to obtain a test sample.

(6) mixing 10 parts by volume of acetic acid buffer, 1 part by volume of 20 mM $FeCl_3.6H_2O$ aqueous solution and 1 part by volume of TPTZ solution, and placing the mixture in water bath at 37° C. for 5 mins.

Acetic acid buffer (pH 3.6, 300 mM): 16.8 g of glacial acetic acid and 0.8 g of sodium hydroxide were mixed with water to prepare a 1 liter solution.

TPTZ solution: an aqueous solution containing 10 mM 2,4,6-tripyridyltriazine and 40 mM hydrochloric acid.

(7) After the completion of step (6), mixing 4 mL of the solution and 30 μL sample to be tested, the mixture was placed for reaction at 37° C. for 120 mins, then measuring absorbance at 593 nm. Standard curve was made using Trolox as a standard sample.

The detection results of flavonoid content, anthocyanin content and antioxidant capacity (also known as antioxidant content) of each of the materials to be tested were shown in Table 2. The results showed that the flavonoid content, anthocyanin content and antioxidant capacity of the flesh of fully red-fleshed plants bred by a cross with 'CSR6R6-777' as a parental plant were significantly higher than those of their parental plant 'Gala'. 'Hongxin 11' and 'Hongxin 16' were sour and sweet, crisp and juicy, fresh, and had good quality. 'Zixia 1', 'Zixia 2' and 'Zixia 3' could be used as raw materials for deep processing. Therefore, 'CSR6R6-777' is a valuable germplasm for functional apple breeding.

TABLE 2

|  | Flavonoid content (mg/kg) | Anthocyanin content (mg/kg) | Antioxidant capacity (μmol/g) |
| --- | --- | --- | --- |
| Zixia 1 | 5055.4 | 218.9 | 4.73 |
| Zixia 2 | 4772.0 | 215.4 | 3.69 |
| Zixia 3 | 1895.2 | 273.4 | 2.66 |
| Hongxin 16 | 8523.3 | 449.4 | 4.30 |
| Hongxin 11 | 349.3 | 46.3 | 1.38 |
| CSR6R6-777 | 7555.1 | 536.6 | 3.89 |
| Gala | 74.6 | 5.2 | 0.16 |

Comparative Example

The 'CSR6R6-777' was replaced with control plant I and the procedure of step I in Example 2 was performed. In August 2016, no fully red-fleshed plant was obtained from the backcross progeny, and only one plant with red and white flesh (tested as R6R1 genotype) was obtained and named as 'Hongza No. 1'.

The 'CSR6R6-777' was replaced with control plant II and the procedure of Step I in Example 2 was performed. In August 2016, no fully red-fleshed plant was obtained from the backcross progeny, and only one plant with red and white flesh (tested as R6R1 genotype) was obtained and named as 'Hongza No. 2'.

The flavonoid content, anthocyanin content and antioxidant capacity of 'Hongza No. 1' and 'Hongza No. 2' were detected in accordance with the method of step IV in Example 2, and the results were shown in Table 3.

Example 3. Fully Red-Fleshed Plants were Obtained by a Cross Using 'CSR6R6-777' as a Parental Plant Apple 'Gala was replaced with apple 'Red Fuji' and the procedure of step I in Example 2 was performed.

In August 2016, four fully red-fleshed plants were selected and cultivated from the backcross progeny population: 'Zixia 4', 'Zixia 5', 'Zixia 6' and 'Hongxin 35'. After detection, 'Zixia 4', 'Zixia 5', 'Zixia 6' and 'Hongxin 35' all had R6R1 genotype.

The flavonoid content, anthocyanin content and antioxidant capacity of 'Zixia 4', 'Zixia 5', 'Zixia 6' and 'Hongxin 35' were detected in accordance with the method of step IV in Example 2, and the results were shown in Table 3.

TABLE 3

|  | Flavonoid content (mg/kg) | Anthocyanin content (mg/kg) | Antioxidant capacity (μmol/g) |
| --- | --- | --- | --- |
| Zixia 4 | 4685.6 | 248.3 | 4.57 |
| Zixia 5 | 4589.2 | 238.1 | 3.86 |
| Zixia 6 | 3976.8 | 275.4 | 2.71 |
| Hongxin 35 | 8213.3 | 452.1 | 4.26 |
| Red Fuji | 81.2 | 6.1 | 0.18 |
| Hongza No. 1 | 136.1 | 10 | 0.25 |
| Hongza No. 2 | 187.6 | 26 | 0.29 |

INDUSTRY APPLICATION

The invention provides apple CSR6R6-777, the flavonoid content and anthocyanin content are high and antioxidant capacity is strong in the flesh of the produced apple fruit, which adds functional health-care effect on basis of the eating quality of the common apple, and may have beneficial effect on the health of people who eats the apple for a long time. The apple fruit produced by apple CSR6R6-777 is used as a raw material to produce apple wine/apple vinegar and the like, which makes the apple wine and the apple vinegar have higher content of flavonoid and anthocyanin, so the health care effect is achieved. The apple CSR6R6-777 provided by the present invention can also be used as a parental plant to cross with other varieties, so that more new high-flavonoid apple germplasm may be obtained, which has great value for high-flavonoid apple breeding.

The invention claimed is:

1. A method for breeding apple elite germplasm, comprising:
   (a) obtaining a hybrid F1 population by crossing a *M. sieversii f. niedzwetzkyana* red flesh apple as a parent plant with a Red Fuji white flesh apple,
   (b) identifying the apple elite germplasm from the hybrid F1 population based on phenotypes and a genotype, wherein the apple elite germplasm is identified as apple *Malus domestica* germplasm CSR6R6-777, of which a representative sample was deposited with the China General Microbiological Culture Collection Center under accession number CGMCC NO. 12468.

2. A method for breeding apple plants, comprising the steps:
   a) crossing an apple variety A with an apple variety B to obtain hybrid seeds;
   wherein the apple variety A is apple *Malus domestica* germplasm CSR6R6-777, of which a representative sample is deposited with the China General Microbiological Culture Collection Center under accession number CGMCC NO. 12468, and the apple variety B is an apple variety other than the apple variety A;
   b) sowing the hybrid seeds obtained in step (a) to obtain seedlings;
   c) transplanting the seedlings obtained in the step (b) to a field, skipping bagging after fruiting, and after screening, obtaining a target plant.

3. The method according to claim 2, wherein in the fourth year after transplanting, the trunk of each of the seedlings is girdled 20 cm away from the ground, and the width of the girdling is 0.5-1.0 cm, and reaching the xylem.

4. The method according to claim 2, wherein in the fifth year after transplanting, the following operations are carried out in the full flowering phase of the seedling: only the central flower among 5 flowers of each of inflorescences is retained, and the rest are all removed.

5. The method according to claim 2, wherein the apple variety B is 'Gala' apple or 'Red Fuji' apple.

6. The method according to claim 2, wherein the apple variety B is an apple variety with R1R1 genotype, wherein the R1R1 genotype is determined as follows:
   obtaining an apple from an apple plant to be tested, extracting genomic DNA from the apple flesh, performing a PCR amplification on the extracted genomic DNA by using a specific primer pair F1 and R1 having the nucleotide sequences as set forth in SEQ ID NO: 1 and SEQ ID NO: 2, respectively;
   wherein the presence of a 386 bp PCR fragment and not a 497 bp PCR fragment in the amplified PCR product indicates that the apple plant to be tested is one with R1R1 genotype.

7. The method according to claim 2, wherein the apple variety B is an apple variety with R1R1 genotype, wherein the R1R1 genotype is determined as follows:
   obtaining an apple from an apple plant to be tested, extracting genomic DNA from the apple flesh, performing a PCR amplification on the extracted genomic DNA by using a specific primer pair F1 and R1 having the nucleotide sequences as set forth in SEQ ID NO: 1 and SEQ ID NO: 2, respectively;
   wherein the presence of a 386 bp PCR fragment in the amplified PCR product indicates that the apple plant to be tested is one with R1R1 genotype.

8. The method according to claim 2, wherein the target plant is a fully red-fleshed plant.

9. The method according to claim 2, wherein the target plant is a fully red fleshed plant with R6R1 genotype, wherein the R6R1 genotype is determined as follows:
   obtaining an apple from an apple plant to be tested, extracting genomic DNA from the apple flesh, performing a PCR amplification on the extracted genomic DNA by using a specific primer pair F1 and R1 having the nucleotide sequences as set forth in SEQ ID NO: 1 and SEQ ID NO: 2, respectively;
   wherein the presence of a 497 bp PCR fragment and a 386 bp PCR fragment in the amplified PCR product indicates that the apple plant to be tested is one with R6R1 genotype.

10. The method according to claim 2, wherein the target plant obtained from step (c) has one or more of the following characteristics:
    (a) fully red-fleshed;
    (b) high-flavonoid content in the flesh;
    (c) high anthocyanin content in the flesh; and
    (d) high antioxidant capacity of the flesh.

11. A method for manufacturing food with apple fruit used as raw material, said method comprising obtaining a plant or a part thereof of apple *Malus domestica* germplasm CSR6R6-777, of which a representative sample was deposited with the China General Microbiological Culture Collection Center under accession number CGMCC NO. 12468.

12. The method of claim 11, wherein a food processing product is manufactured.

13. The method of claim 1, wherein when genomic DNA from the apple *Malus domestica* germplasm CSR6R6-777 is amplified by polymerase chain reaction (PCR) using F1 primer having sequence 5'-GGTGGTCAAA-GATGTGTGTTGT-3' (SEQ ID NO: 1) and R1 primer having sequence 5'-TTTGCCTGCTACCCACTTCA-3' (SEQ ID NO: 2), there is one band for the PCR amplified product with a size of 497 bp.

\* \* \* \* \*

SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: F1 primer

<400> SEQUENCE: 1
ggtggtcaaa gatgtgtgtt gt                                          22

<210> SEQ ID NO 2
<211> LENGTH: 20
<212> TYPE: DNA
<213> ORGANISM: Artificial Sequence
<220> FEATURE:
<223> OTHER INFORMATION: R1 primer

<400> SEQUENCE: 2
tttgcctgct acccacttca                                             20

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
ggagacaact ggagaaggac tggaa                                       25

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
cgacattgat actggtgtct tc                                          22

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
tggaagcttg tgaggactgg ggt                                         23

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
ctcctccgat ggcaaatcaa aga                                         23

<210> SEQ ID NO 7
<211> LENGTH: 21
<212> TYPE: DNA
<213> ORGANISM: Artificial Sequence -continued

```
<220> FEATURE:
<223> OTHER INFORMATION: primer

<400> SEQUENCE: 7
ccaagtgaag cgggttgtgc t                                                 21

<210> SEQ ID NO 8
<211> LENGTH: 23
<212> TYPE: DNA
<213> ORGANISM: Artificial sequence
<220> FEATURE:
<223> OTHER INFORMATION: primer

<400> SEQUENCE: 8
caaagcaggc ggacaggagt agc                                               23

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
caccgtcaag tccttcaa                                                     18

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
acctcttaac tgtaccaact g                                                 21

<210> SEQ ID NO 11
<211> LENGTH: 20
<212> TYPE: DNA
<213> ORGANISM: Artificial sequence
<220> FEATURE:
<223> OTHER INFORMATION: primer

<400> SEQUENCE: 11
aaccactgtg aacaaggata                                                   20

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
catagtcgcc gtacttctt                                                    19

<210> SEQ ID NO 13
<211> LENGTH: 23
<212> TYPE: DNA
<213> ORGANISM: Artificial sequence
<220> FEATURE:
<223> OTHER INFORMATION: primer

<400> SEQUENCE: 13
tgcctggact cgagaggaag aca                                               23
```

```
<210> SEQ ID NO 14
<211> LENGTH: 23
<212> TYPE: DNA
<213> ORGANISM: Artificial sequence
<220> FEATURE:
<223> OTHER INFORMATION: primer

<400> SEQUENCE: 14
cctgtttccc aaaagcctgt gaa                                              23
```